United States Patent
Gidekel et al.

(10) Patent No.: US 10,058,582 B2
(45) Date of Patent: Aug. 28, 2018

(54) THERAPEUTIC MOLECULES AND DEVIATES FOR CRC

(71) Applicant: ANTARTINA LLC, Santiago (CL)

(72) Inventors: Manuel Gidekel, Santiago (CL); Julio Alvarez Builla, Madrid (ES); Guillermo Mazzolini, Escobar (AR)

(73) Assignee: Antartina LLC, Dover, DE (US)

( * ) Notice: Subject to any disclaimer, the term of this patent is extended or adjusted under 35 U.S.C. 154(b) by 0 days.

(21) Appl. No.: 15/236,115

(22) Filed: Aug. 12, 2016

(65) Prior Publication Data

US 2017/0049839 A1    Feb. 23, 2017

Related U.S. Application Data

(60) Provisional application No. 62/283,137, filed on Aug. 20, 2015.

(51) Int. Cl.
*A61K 31/7048* (2006.01)
*A61K 36/899* (2006.01)

(52) U.S. Cl.
CPC ........ *A61K 36/899* (2013.01); *A61K 31/7048* (2013.01)

(58) Field of Classification Search
None
See application file for complete search history.

(56) References Cited

PUBLICATIONS

Guo et al., Journal of Food Biochemistry, 37(4), 2013, pp. 501-509.*

* cited by examiner

*Primary Examiner* — Traviss C McIntosh, III
(74) *Attorney, Agent, or Firm* — John Dodos

(57) ABSTRACT

The chemically synthesized compound Tricin 7-O-beta-D-glucopyranoside, native to the plant *Deschampsia Antarctica* and present in aqueous extracts of the plant *Deschampsia Antarctica* said compound having the ability to inhibit tumor growth in mammals with colorectal carcinoma.

3 Claims, 15 Drawing Sheets

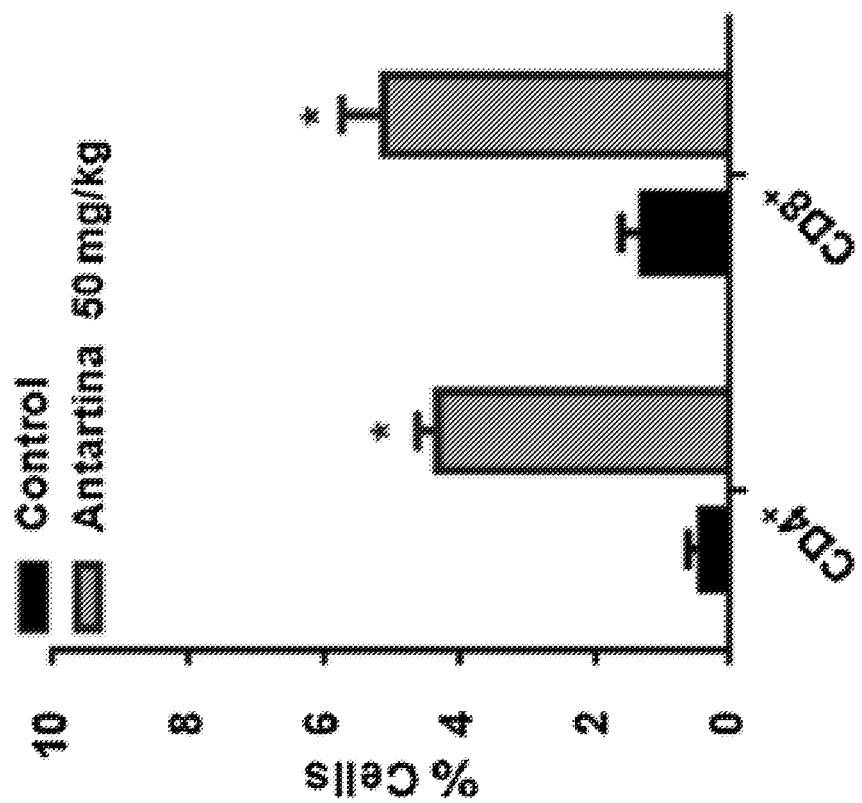

THERAPEUTIC MOLECULES AND DEVIATES FOR CRC

This application claims priority a filing date of Aug. 20, 2015 based on U.S. Provisional Patent Application 62/283,137

The Antarctic continent has emerged in the last decade as a fertile location for scientists aiming to discover and develop new biotechnological applications. With its unique weather and environmental characteristics, Antarctica is home to an extraordinary variety of extremophile organisms, especially bacteria and fungi, and two remarkable vascular plants, *Colobanthus quitensis* and *Deschampsia antarctica* (cita). There are several examples of novel psychrophile enzymes and new molecules isolated from organisms found in Antarctica with potential uses in agriculture, medicine, and a variety of industries (citas).

Cancer is one of the main causes of death in the world with 14.1 million new cases in 2012 (Globocan). Until now intensive efforts worldwide have increased our understanding on the molecular mechanisms causing diverse types of cancer, but the prognosis is mostly dependent on the time of diagnosis; sadly late-diagnosis cases an incurable disease. Cancer treatment usually involves a combination of procedures including surgery, radiotherapy, chemotherapy, and biological agents; however, some of them are very aggressive. Despite the relative success in cancer therapy, especially in early diagnosis cases, cancer now causes worldwide more deaths than all coronary heart disease or all stroke (WHO report, 2000-2012).

*D. antarctica* is capable of tolerating high UV exposure due to the production of secondary metabolites as photoprotector agents, especially flavonoid-like molecules (Alberdi et al. 2002, Barcikowski et al. 1999, Bravo and Griffith, 2005, Ruhland and Day, 2001 van de Staaij et. al. 2002, Webby and Markham, 1994). We have found anticancer effects in an aqueous extract of dried *D. Antarctica*, and in this patent we describe the first chemically synthetized component of the extract, the Antartina, with anticancer activity in several cell cancer types. This is the first chemically synthesized and results show it retains the anticancer activity in several cell cancer types. In this application we show that, systemic injection of this compound in mice with colorectal carcinoma demonstrated a potent anticancer effect without any obvious sign of toxicity. These findings identify Antartina as an unexpected anticancer agent, and suggest that this molecule can be used as a new anticancer agent with potential uses in a broad spectrum of cancer types.

Experimental Procedure

Melting points determined in open capillary tubes with a Stuart Scientific SMP3 melting point apparatus. IR spectra obtained with a Perkin-Elmer FTIR spectrum 2000 or Perkin-Elmer Frontier spectrophotometers, 1H and 13C NMR spectra were recorded using Varian Gemini 200, Varian Unity 300/500 MHz or Varian Mercury 300/400 systems at room temperature. Chemical shifts are given in ppm ($\delta$) downfield from TMS. Coupling constants (J) are in Hertz [Hz] and signals are described as follows: s, singlet; d, doublet; t, triplet; q, quadruplet; m, multiplet; br, broad; app, apparent. HPLC-MS were recorded on an Agilent 1100 MSD-Q yielding the ESI. High-resolution analysis (TOF) was performed using an Agilent 6210 time-of-flight LC/MS. All reagents were obtained from commercial sources and were used without further purification. TLC analyses ere performed using silica gel (Kieselgel 60 F254, Macherey-Nagel) and spots were visualized under UV light. Column chromatography was carried out with silica gel 60 (40-63 µm, Merck) columns, using the eluent reported in each case.

1-[2-Hydroxy-4-(methoxymethoxy)-6-benzyloxyphenyl]-3-(4-benzyloxy-3,5-dimethoxyphenyl)propenone 3. To a suspension of sodium hydride (583 mg, 60% dispersion in mineral oil) in heptane (1-3 mL) under nitrogen, with stiffing, dry DMF (ab 3 mL) was added, and the white suspension was cooled in an ice bath. A solution of 2-benzyloxy-4-(methoxymethoxy)-6-hydroxyacetophenone $1^1$ (2 g) in dry DMF (16 mL) was slowly added. The mixture was stirred for 30 min while cooling in an ice-water bath. The, a solution of 4-benzyloxy-3,5-dimethoxybenzaldehyde $2^{2,3}$ (1.9 g) in dry DMF (16 mL) was drop-wise added. The reaction mixture was stirred for additional 10 min, at 0° C. and for 2 h at room temperature. The reaction was then poured onto crushed ice (125 g) and pH was adjusted to 7.0 with 1M HCl (ab 23 mL). The aqueous phase was extracted with EtOAc (ab 250 mL) and then, the organic layer was washed with sat. aqueous ammonium chloride (2×100 mL). The combined organic solution was dried over $Na_2SO_4$, filtered and evaporated to dryness. The residue was purified by silica gel column chromatography (Hexane/EtOAc) to give compound 3 (3.5 g, 95% yield) as a yellow solid, mp 70-77.6° C. IR (KBr, $cm^{-1}$): 3090, 2922, 1629, 1583, 1322, 1277, 1156, 1127, 730, 694. $^1$H-NMR (CDCl$_3$, 500 MHz, $\delta$): 3.53 (s, 3H), 3.65 (s, 6H), 5.09 (s, 2H), 5.16 (s, 2H), 5.25 (s, 2H), 6.24 (d, 1H, J=2.4 Hz), 6.35 (d, 1H, J=2 Hz), 6.61 (s, 2H), 7.25-7.40 (m, 6H), 7.45 (dd, 2H, J=1.5 Hz, 4.5 Hz), 7.51 (dd, 2H, J=1.5H, 4.5 Hz), 7.72 (d, 1H, J=15.7 Hz), 7.82 (d, 1H, J=15.7 Hz) ppm. $^{13}$C-NMR (CDCl$_3$, 125 MHz, $\delta$): 55.9 (2), 56.3, 71.0, 74.9, 92.8, 94.0, 96.8, 105.7 (2), 126.9, 127.1 (2), 127.9, 128.1 (2), 128.2, 128.4 (2), 128.65 (3), 130.7, 135.6, 137.4, 142.6, 153.4 (2), 161.5, 163.5, 167.5, 192.6 ppm. HRMS (ESI-TOF): m/z calcd. for $C_{33}H_{32}O_8$: 556.2097; found, 556.2075.

5-benzyloxy-2-(4-benzyloxy-3,5-dimethoxy-phenyl)-7-(methoxymethoxy)chroman-4-one 4. To a suspension of compound 3 (19 g) in MeOH (125 mL), sodium acetate (28 g) was added and refluxed for 10-20 h, until no starting materials were detected. The reaction mixture was evaporated to dryness and extracted between a saturated aqueous sodium bicarbonate solution (500 mL) and EtOAc (500 mL). Phases were separated and the aqueous layer was extracted with EtOAc (500 mL). The combined organic solution was dried over $Na_2SO_4$, filtered and evaporated to dryness. The residue was purified by silica gel column chromatography (Hexane/EtOAc) to give compound 4 (10.3 g, 54.2% yield) as a white solid, mp 141-145° C. IR (KBr,$cm^{-1}$): 1682, 1609, 1461, 1152, 1125, 1110, 742, 698. $^1$H-NMR (CDCl$_3$, 500 MHz, $\delta$): 2.78 (dd, 1H, J=3 Hz, 17 Hz), 3.02 (dd, 1H, J=13 Hz, 17 Hz), 3.45 (s, 3H), 3.84 (s, 6H), 4.99 (s, 2H), 5.15 (s, 2H), 5.18 (s, 2H), 5.32 (dd, 1H, J=3 Hz, 13 Hz), 6.26 (d, 1H, J=2.4 Hz), 6.35 (d, 1H, J=2 Hz), 6.65 (s, 2H), 7.28-7.40 (m, 6H), 7.48 (dd, 1H, J=1 Hz, 7 Hz), 7.58 (dd, 1H, J=1 Hz, 7 Hz) ppm. $^{13}$C-NMR (CDCl$_3$, 125 MHz, δ): 45.9, 56.2 (2), 56.4, 70.4, 75.0, 79.4, 94.1, 95.6, 96.4, 103.3 (2), 107.0, 126.6 (2), 127.7, 127.8, 128.14 (2), 128.4 (2), 128.5 (2), 134.4, 136.3, 137.2, 137.7, 153.8(2), 161.1, 163.4, 164.5, 189.0 ppm. HRMS (ESI-TOF): m/z calcd. for C$_{33}$H$_{32}$O$_8$: 556.2097; found, 556.2078.

5-benzyloxy-2-(4-benzyloxy-3,5-dimethoxy-phenyl)-7-(methoxymethoxy)chromen-4-one 5. To a solution of compound 4 (3.5 g) in dry pyridine (90 mL), iodine (1.6 g) was added, and the mixture heated to 90° C. for 10-20 h. The reaction was then poured onto cold water and pH was adjusted to ab. 6 with 5% HCl (ab. 135 mL). The aqueous phase was extracted with EtOAc (2×200 mL) and the organic layer was washed successively, with saturated sodium thiosulfate (2×200 mL) and brine (200 mL) The combined organic solution was dried over Na$_2$SO$_4$, filtered and evaporated to dryness to give compound 5 (3.4 g, quantitative) as a brown solid, which was used in next step without further purification, mp 122-125° C. IR (KBr, cm$^{-1}$): 1645, 1609, 1500, 1454, 1419, 1348, 1261, 1128, 802. $^1$H-NMR (DMSO-d$_6$, 500 MHz, δ): 3.42 (s, 3H), 3.90 (s, 6H), 4.99 (s, 2H), 5.23 (s, 2H), 5.34 (s, 2H), 6.29 (d, 1H, J=2 Hz), 6.86 (s, 1H), 6.98 (d, 1H, J=2.4 Hz), 7.29 (s, 2H), 7.29-7.46 (m, 8H), 7.60 (d, 1H, J=7.4 Hz) ppm. $^{13}$C-NMR (DMSO-d$_6$, 125 MHz, δ): 55.3, 55.5(2), 69.1, 73.2, 93.1, 95.2, 97.9, 102.8(2), 107.4, 108.4, 125.5, 126.1(2), 126.7, 127.0, 127.2(2), 127.3(2), 127.5(2), 136.0, 136.7, 138.2, 152.6(2), 158.0, 158.2, 158.7, 160.1, 175.0 ppm. HRMS (ESI-TOF): m/z calcd. for C$_{33}$H$_{30}$O$_8$; 554.1941; found, 554.1923.

5-benzyloxy-2-(4-benzyloxy-3,5-dimethoxy-phenyl)-7-hydroxy-chromen-4-one 6. To a suspension of compound 5 (10.36 g) in MeOH (190 mL), aq. 3N HCl (ab. 190 mL) was added, and the mixture heated to 60° C. for 18 h. Solvents were evaporated and the remaining solid was filtered and washed with water (2×100 mL) to give compound 6 (9.5 g, quantitative) as a brown solid, which was used in the next step without further purification, mp 199-205° C. IR (KBr, cm-1): 3400, 2962, 1622, 1589, 1564, 1354, 1162, 1128, 833. $^1$H-NMR (DMSO-d$_6$, 500 MHz, δ): 3.89 (s, 6H), 4.99 (s, 2H), 5.19 (s, 2H), 6.47 (d, 1H, J=2 Hz), 6.64 (d, 1H, J=2 Hz), 6.78 (s, 1H), 7.26 (s, 2H), 7.29-7.46 (m, 8H), 7.60 (d, 1H, J=7.4 Hz) ppm. $^{13}$C-NMR (DMSO-d$_6$, 125 MHz, δ): 55.8(2), 69.2, 73.5, 95.3, 97.5, 103.3(2), 107.1, 107.5, 126.0, 126.4(2), 127.0, 127.3, 127.5(2), 127.6(2), 127.8(2), 136.4, 137.0, 138.3, 152.9(2), 158.5, 158.7, 158.8, 161.9, 175.2 ppm. HRMS (ESI-TOF): m/z calcd. for C$_{33}$H$_{30}$O$_8$: 554.1941; found, 554.1923.

5-benzyloxy-2-(4-benzyloxy-3,5-dimethoxy-phenyl)-7-(2,3,4,6-tetra-O-acetyl-β-D-glucopyranosyl)-chromen-4-one 7. To a mixture of compound 6 (0.5 g), TBAB (0.053 g), and 2,3,4,6-tetra-O-acetyl-α-D-glucopyranosyl bromide 11 (0.806 g) in chloroform (25 mL), 0.25M potassium carbonate solution (8.6 mL) was added and the reaction mixture was heated to 45° C. for 10-20 h. (More equivalents of sugar were sometimes needed). The reaction mixture was warmed to room temperature and the phases were separated. Then, the aqueous layer was extracted with dichloromethane (2×100 mL) and the combined organic solution was evaporated to dryness. The residue was purified by silica gel column chromatography (Hexane/EtOAc) to give compound 13 (0.5 g, 61% yield) as a clear yellow solid, mp 170-173° C. IR (KBr, cm$^{-1}$): 1759, 1650, 1609, 1347, 1177, 1128, 1064, 1038, 739, 698. $^1$H-NMR(CDCl$_3$, 500 MHz, δ): 1.99 (s, 3H), 2.03 (s, 6H), 2.04 (s, 3H), 3.89 (s, 6H), 3.95 (m, 1H), 4.12 (dd, 1H J=2.5 Hz, 12.2 Hz), 4.26 (dd, 1H J=5.4 Hz, 12.2 Hz), 5.07 (s, 2H), 5.15 (m, 2H), 5.24-5.32 (m, 2H), 5.25 (s, 2H), 6.46 (d, 1H, J=2 Hz), 6.63 (s, 1H), 6.65 (d, 1H, J=2 Hz), 7.03 (s, 2H), 7.24-7.46 (m, 6H), 7.46 (d, 1H, J=6.8 Hz), 7.57 (d, 1H, J=6.8 Hz) ppm. $^{13}$C-NMR (CDCl$_3$, 125 MHz, δ): 20.5(2), 20.6(2), 56.4(2), 61.9, 68.1, 70.9, 71.0, 72.1, 72.4, 75.1, 96.8, 97.9, 99.0, 103.7(2), 108.8, 111.0, 126.5(2), 126.6, 127.8, 128.0, 128.2(2), 128.4(2), 128.6(2), 136.0, 137.3, 139.9, 153.8(2), 159.2, 159.9, 160.4, 161.0, 169.3, 169.3, 170.1, 170.4, 177.1 ppm. HRMS (ESI-TOF): m/z calcd. for C$_{45}$H$_{44}$O$_{16}$: 840.2629; found, 840.2616.

5-hydroxy-2-(4-hydroxy-3,5-dimethoxy-phenyl)-7-(2,3,4,6-tetra-O-acetyl-β-D-glucopyranosyl)-chromen-4-one 8. To a solution of compound 7 (0.4 g) in Ethanol/EtOAc 1:1 (30 mL), 10% palladium on charcoal (40 mg) was added, and the reaction mixture was stirred at room temperature under hydrogen atmosphere (ab 2.0 bar) for 18-48 h. The catalyst was filtered through Celite®. The filter pad was rinsed with ethanol and THF and the filtrate was evaporated to dryness to yield compound 8 (0.3 g, quantitative) as a brown solid, mp 120-124° C. IR (KBr, cm$^{-1}$): 3437, 1753, 1615, 1225, 1040, 842. $^1$H-NMR (DMSO-d$_6$, 500 MHz, δ): 1.99 (s, 9H), 3.89 (s, 6H), 4.01-5.21 (m, 6H), 5.77 (d, 1H, J=7 Hz), 6.47 (s, 1H), 6.86 (s, 1H), 7.08 (s, 1H), 7.39 (s, 2H,), 13.00 (s, 1H) ppm. $^{13}$C-NMR (DMSO-d$_6$, 125 MHz, δ): 19.5, 19.7(2), 19.7, 54.8, 55.6, 61.2, 62.5, 69.9, 70.3, 70.5, 71.4, 93.2, 95.7(2), 98.3, 104.1(2), 128.1, 131.0, 147.7(2), 156.3, 160.9, 168.6, 168.8(2), 169.1, 169.4, 169.6, 174.7 ppm. HRMS (ESI-TOF): m/z calcd. for C$_{31}$H$_{32}$O$_{16}$: 660.1690: found, 660.1677.

Tricin 7-O-β-D-glucopyranoside or Antarctin 9a. To a suspension of compound 8 (0.7 g) in MeOH (54 mL), a 30% aqueous ammonia solution (24 mL) was added, and the mixture stirred at room temperature for 10-20 h. The mixture was evaporated to dryness and the solid residue was filtered and washed with water (100 mL). Solid was dried to give compound 9a (0.5 g, 95.8% yield) as a clear brown solid, mp 211-214° C. (Lit.[4] 244-6° C.) IR (KBr, cm$^{-1}$): 3369, 1658, 1607, 1496, 1340, 1030, 804. $^1$H-NMR (DMSO-d$_6$, 500 MHz, δ): 3.20-3.80 (m, 3H), 3.88 (s, 6H), 3.95 (m, 1H), 4.12 (dd, 1H J=2.5 Hz, 12.2 Hz), 4.26 (dd, 1H J=5.4 Hz, 12.2 Hz), 5.07 (s, 2H), 4.35 (m, 2H), 4.60 (m, 1H), 5.00-5.18 (m, 3H), 5.40 (s, 1H), 6.44 (s, 1H), 6.92 (s, 1H), 7.05 (s, 1H), 7.21 (s, 2H), 9.33 (s, 1H), 12.94 (s, 1H) ppm. $^{13}$C-NMR (DMSO-d$_6$, 125 MHz, δ): 56.1(2), 60.2, 69.9, 72.6, 76.0, 76.9, 95.4, 96.8, 99.0, 105.0, 107.0, 108.4, 125.4, 137.9, 150.6, 158.2, 159.7, 159.8, 161.0, 175.1. HRMS (ESI-TOF): m/z for C$_{23}$H$_{24}$O$_{12}$: 492.1268; found, 492.1259.

Scheme 1

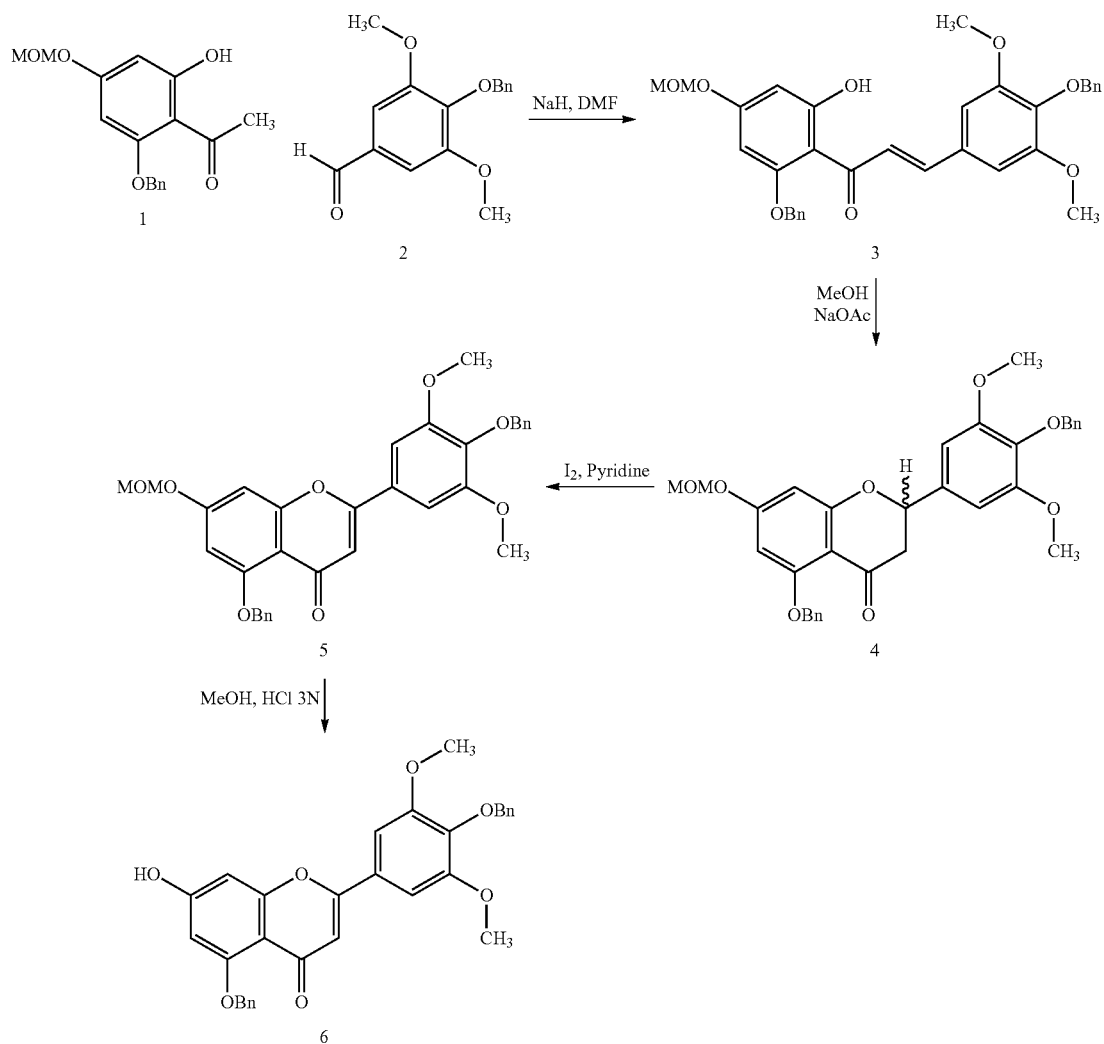

Figure 1:
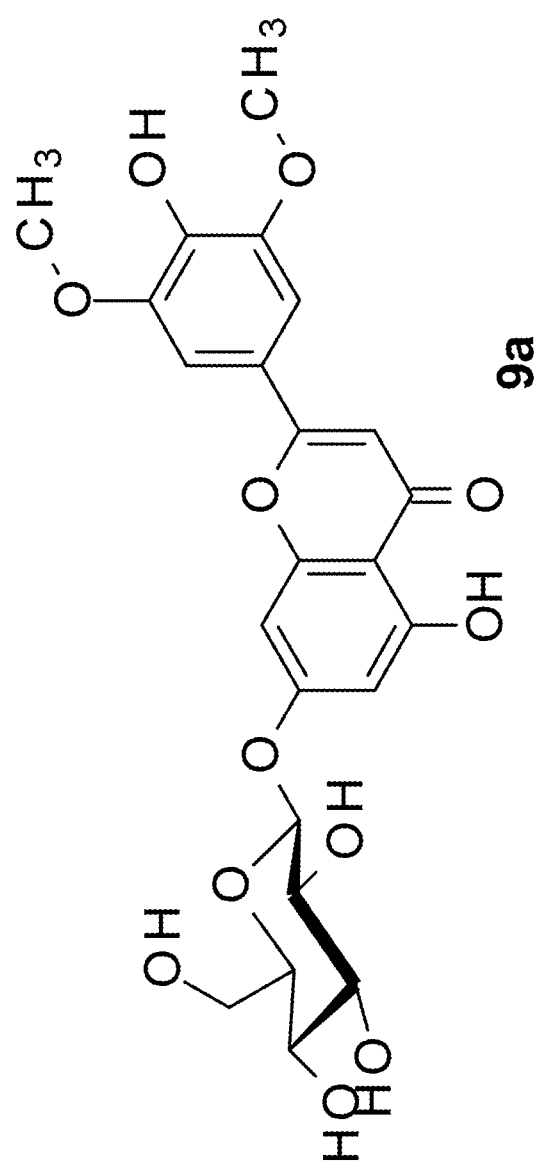
FIG. 1 shows Tricin 7-O-β-D-glucopyranoside 11 (FIG. 1, Antarina) was obtained following the synthetic method indicated in the Schemes 1 and 2.

In the scheme 1, the initial aldol condensation was performed using 2-benzyloxy-4-(methoxymethoxy)-6-hydroxyacetophenone 1 (Kumazawa, T., Minatogawa, T., Matsuba, S., Sato, S., Onodera, J., Carbohydr. Res. 2000, 329, 507-513) with 4-benzyloxy-3,5-dimethoxybenzaldehyde 2, (Bennett, C. J., Caldwell, S. T., McPhail, D. B., Morrice, P. C., Duthie, G. G., Hartley, R. C., Bioorg. Med. Chem., 2004, 12, 2079-2098), (Cushman, M.; Nagarathnam, D.; Gopal, D.; He, H. M.; Lin, C. M.; Hamel, E. J. Med. Chem. 1992, 35, 2293-2306). Then, the chalcone 3, was cyclized through an intramolecular Michael reaction to produce 4, which was oxidized by iodine to generate the more stable compound 5. Finally, treatment of 5 in acid media, yielded the chromenone 6, deprotecting the phenol group in the 7 position.

Scheme 2

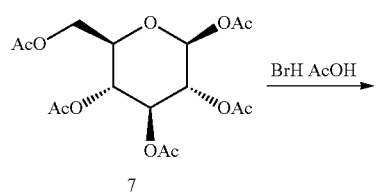

-continued

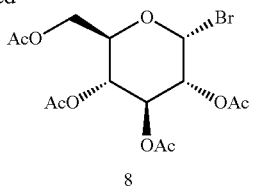

In the scheme 2, the second part of the synthesis of Antarina is described. Initially, the reaction of 2,3,4,6-tetra-O-acetyl-α-D-glucopyranosylbromide 11 (Tokutake, S., Yamaji, N., Kato, M., Chem. Pharm. Bull., 1990, 38, 13-18) with 5-benzyloxy-2-(4-benzyloxy-3,5-dimethoxy-phenyl)-7-hydroxy-chromen-4-one 6, by the use of a phase transfer process, yielding the glucoside 7. Then, the hydrogenation cleaved the benzyl groups to produce 8. Finally, the treatment of 8 with ammonia produced deprotection of the acetyl esters to produce the tricin 7-O-β-D-glucopyranoside 9a or antarctin (Syrchina, A. I.; Vereshchagin, A. L.; Larin, M. F.; Semenov, A. A. Khimiya Prirodnykh Soedinenii, 1989, 725-6).

The product 9a is a flavonoid, detected as a minor component in many described plants as, to name a few, in Pleioblastus amarus Keng f. (Wei, Q.; Yue, Y.; Tang, F.; Sun, J.; Wang, S.; Yu, J.; Tianran Chanwu Yanjiu Yu Kaifa 2014, 26, 38-42), in of *Kummerowia striata*, (Li, S. Zhongguo Yaoxue Zazhi, 2014, 49, 817-820), in *Setaria viridis*, (Fan, L.; Ma, J.; Chen, Y.; Chen, X.; Chemistry of Natural Compounds 2014, 50, 433-437). In *Dendrocalamus latiflorus* (Wang, S.; Yue, Y.; Tang, F.; Sun, J.; Wei, Q.; Yu, J.; Linye Kexue 2013, 49, 135-140). Or in *Ranunculus muricatus* (Nazir, S.; Li, B.; Tahir, K.; Khan, A.; Ul Haq Khan, Z.; Khan, S.; Journal of Medicinal Plants Research 2013, 7, 3438-3443) among others.

Figure 2:
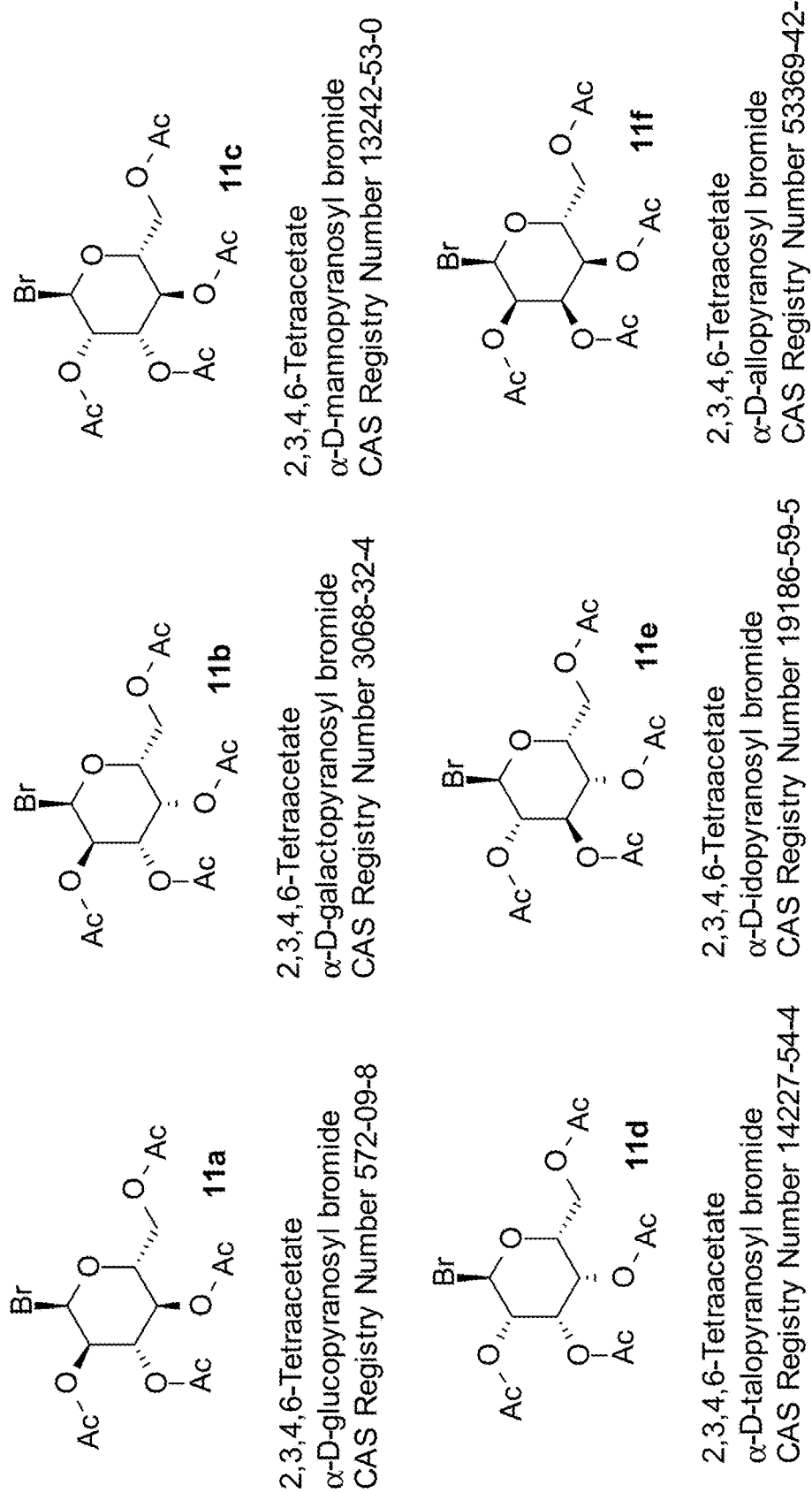

FIG. 2 shows the bromo sugars available.

Figure 3:
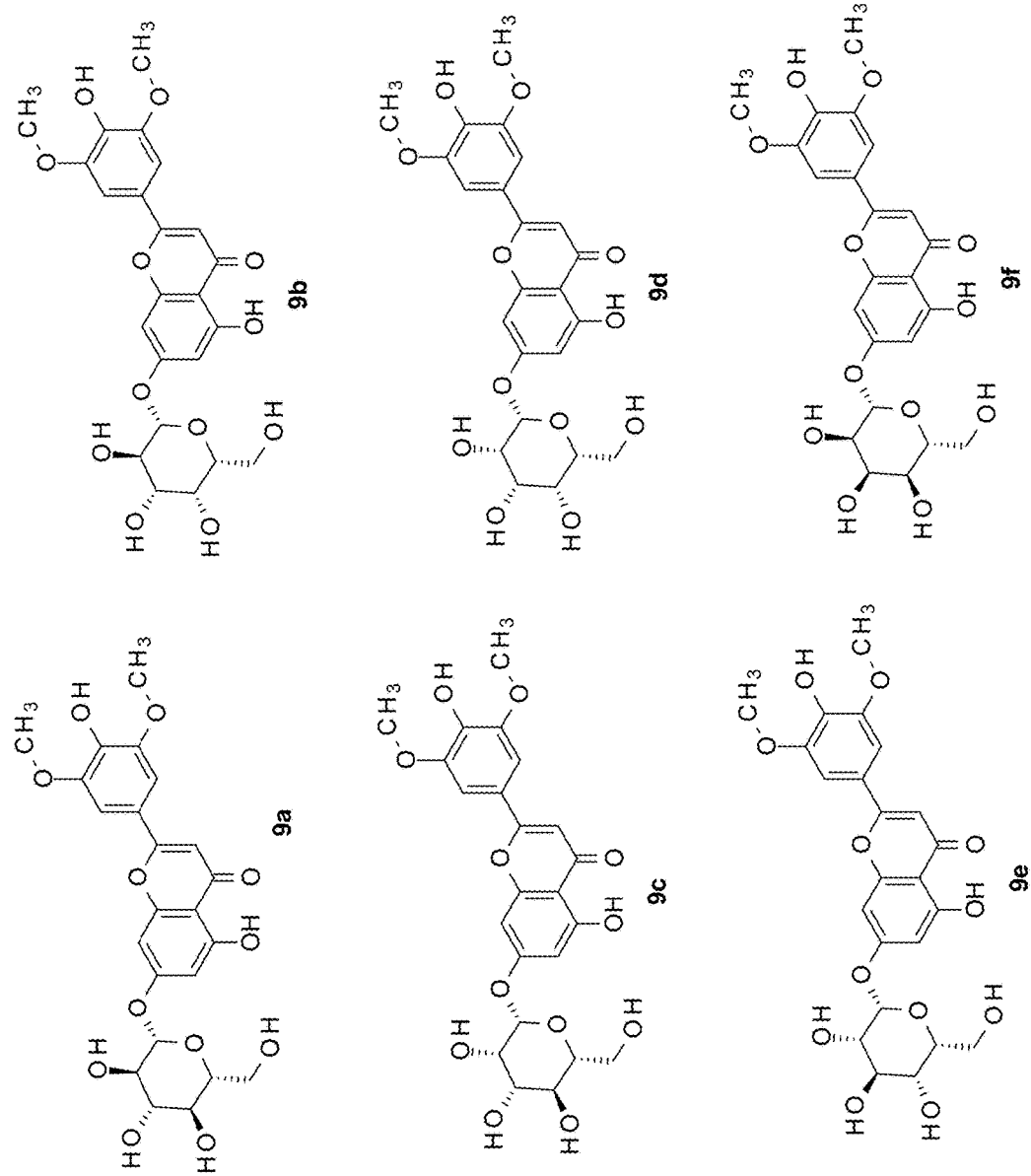

FIG. 3 shows the corresponding flavonoids obtained.

Figure 4:
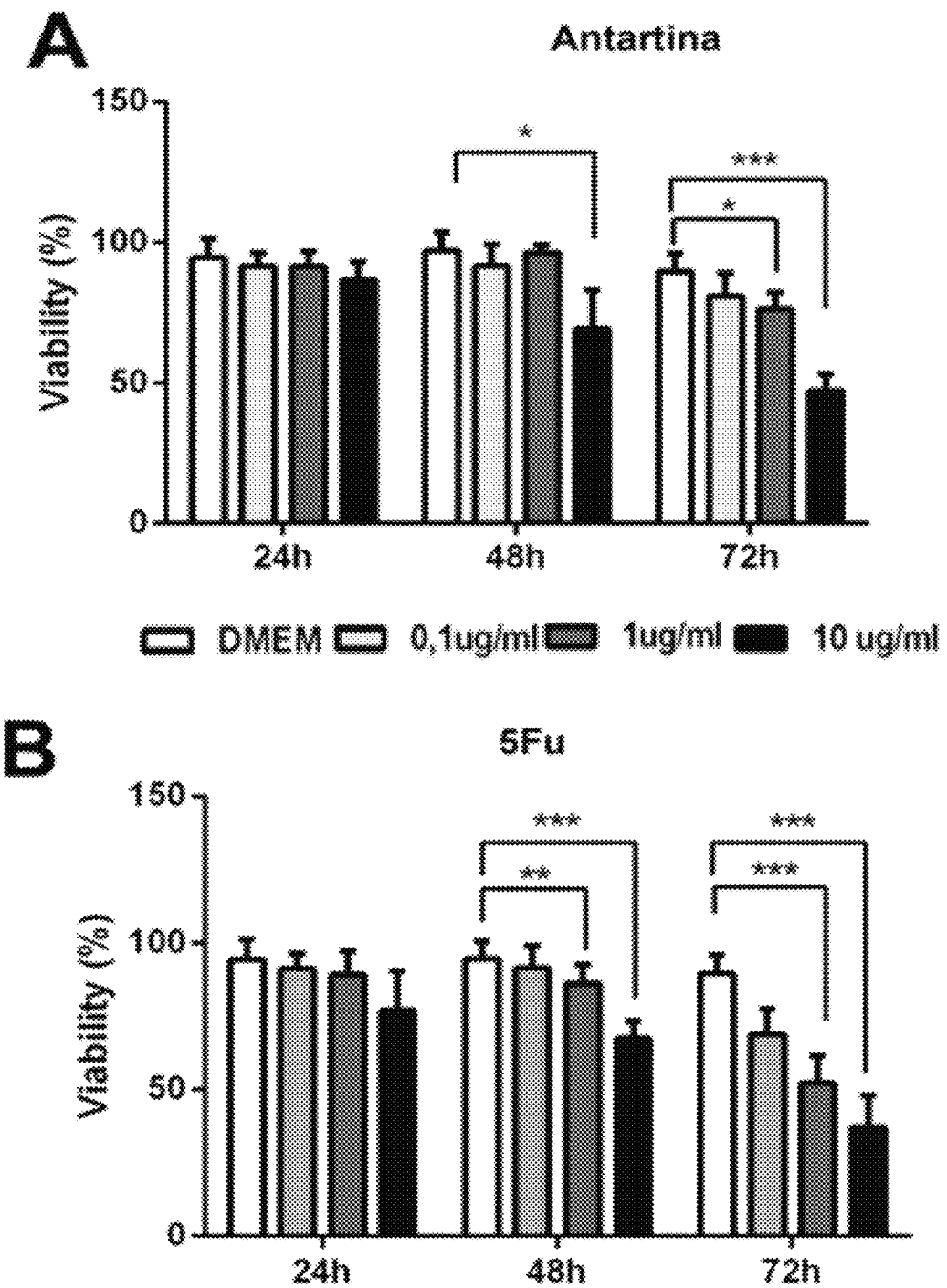
Figure 4:
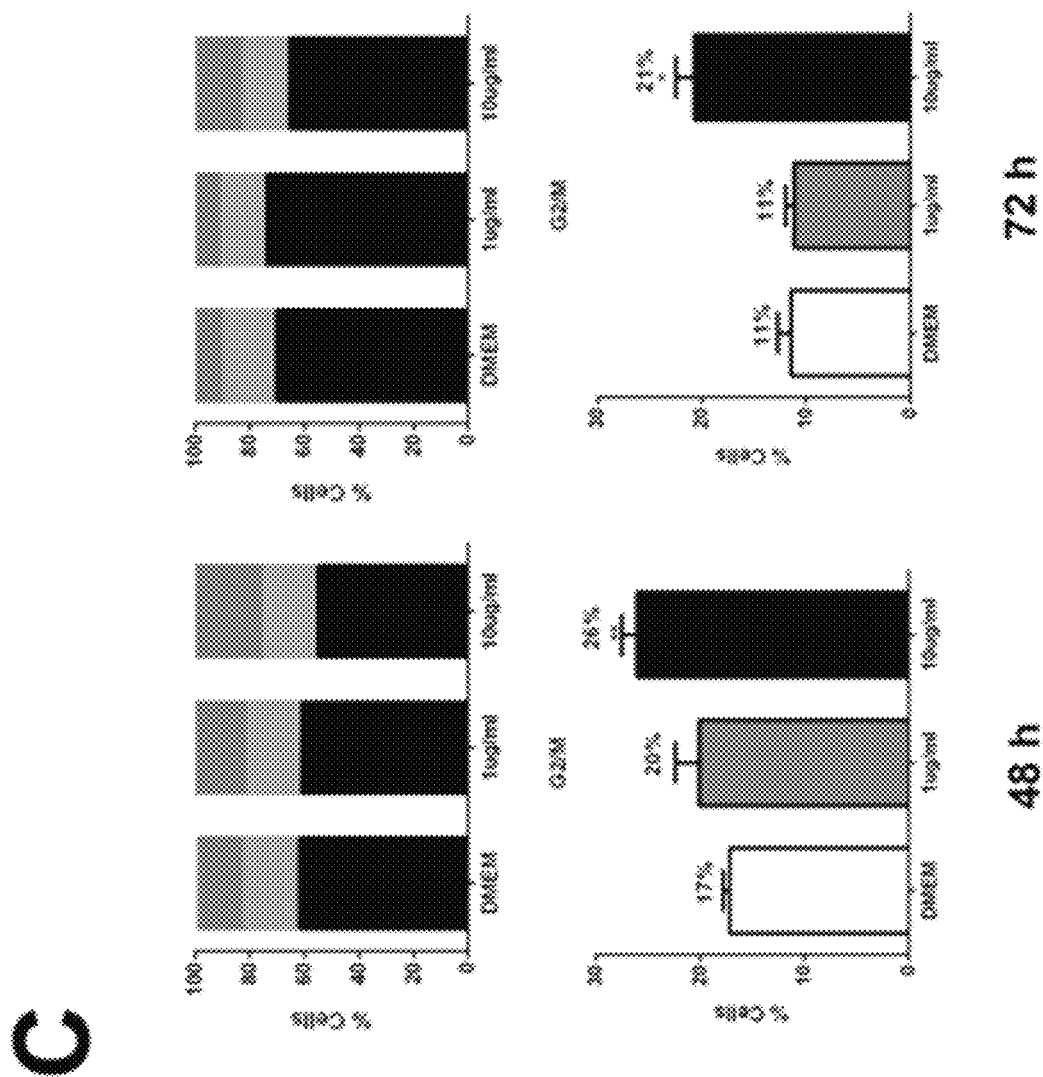
Figure 4:
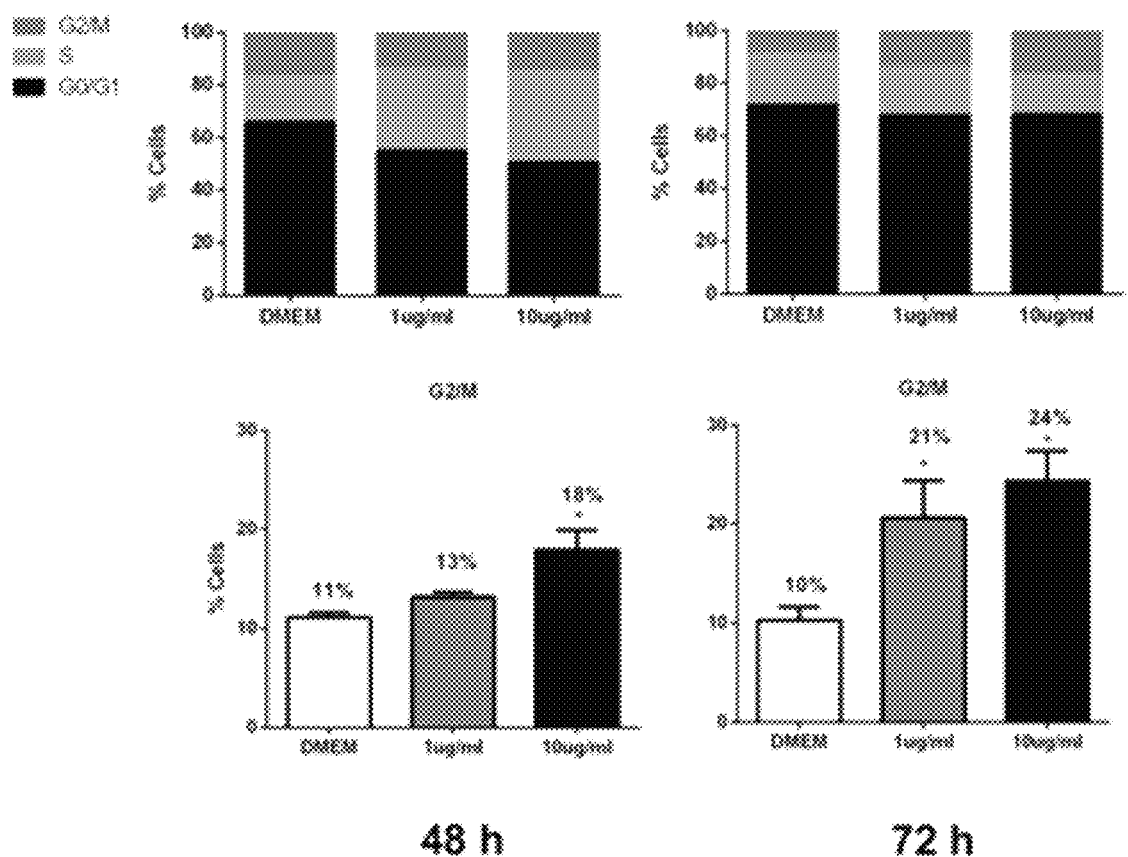

FIG. 4 shows Antarina® inhibits CT26 cells growth in vitro. A) CT26 cells were incubated with DMEM or increasing concentrations of DA during 3 days. Cell viability was determined by MTS assay at 490 nm, in 2 independent studies. *$p<0.05$; ***$p<0.001$ ANOVA and Tukey's test. B) The effect of Antarina® was compared with 5-Fu ability to inhibit CRC cells growth *$p<0.05$; $p<0.01$; *$p<0,001$ using ANOVA and Tukey's test. C) Cell cycle flow cytometry analysis of CT26 cells stained with propidium iodide at 48 and 72 h; Antarina® (10 □g/ml) incubation halted CT26 cells at the transition from G2 to M-phase. **$p<0.01$ or *$p<0.05$ ANOVA and Tukey's test. D) Cell cycle analysis of 5-Fu treated cells *$p<0.05$ ANOVA and Tukey's test.

Figure 5:
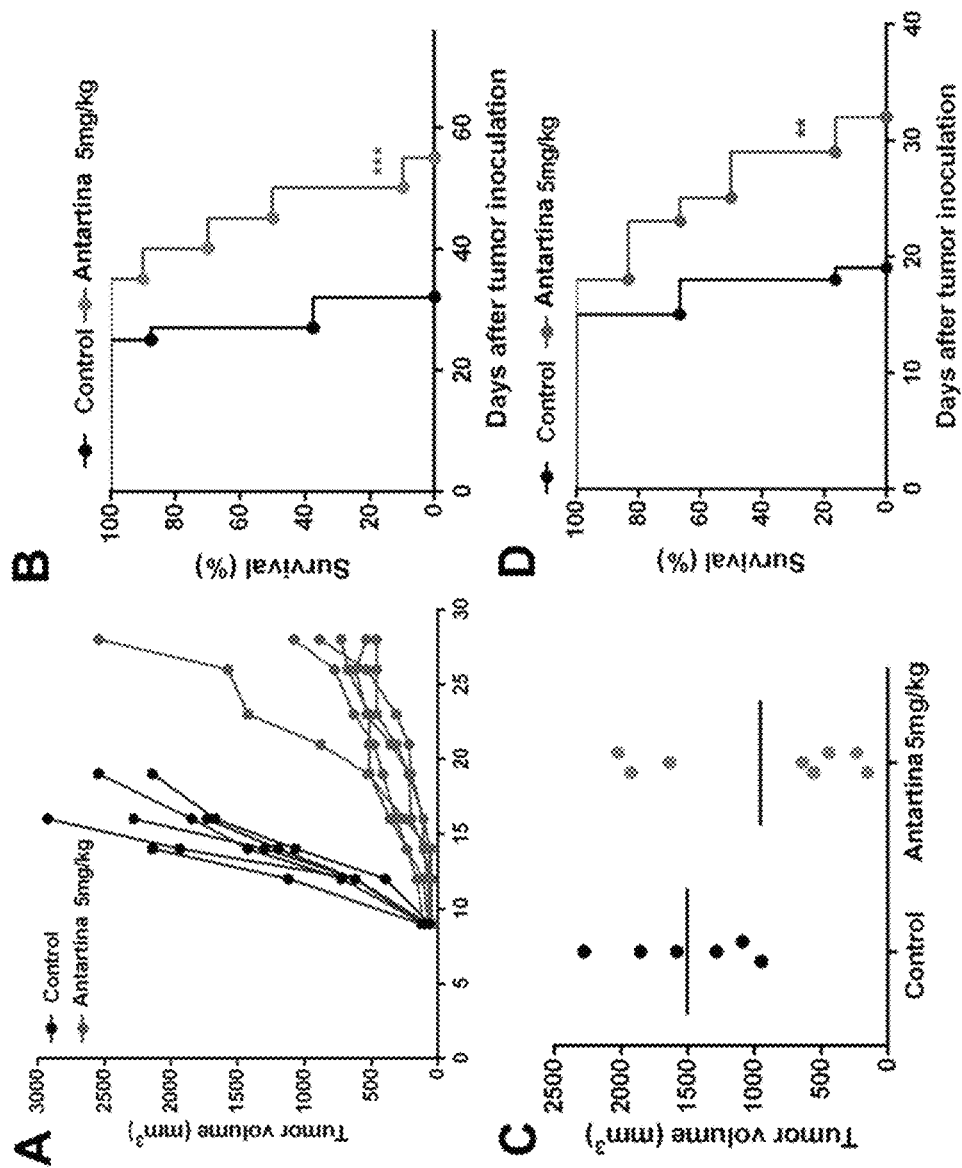

FIG. 5 shows antitumoral activity of Antarina® in CT26 CRC tumor models. A) Subcutaneous model: BALB/c mice were s.c. injected with $5\times10^5$ CT26 cells into the right flank (day 0) and tumors were allowed to reach 90 mm3 before treatment was started. Animals were distributed in groups: saline, Antarina® (5 mg/kg i.p., day 8 three times a week). Data are expressed as mean tumor volume. B) Animal survival after treatment (Kaplan-Meier, log rank test, $P<0.001$). C) Liver CRC metastatic model: BALB/c mice were injected with $5\times10^5$ CT26 cells directly into the liver by laparotomy (day 0). Animals were distributed into different groups: saline, Antarina® (5 mg/kg i.p., day 8 three times a week). Data are expressed as mean tumor volume. D) Animal survival after treatment (Kaplan-Meier, log rank test, $P<0.001$).

Figure 6:
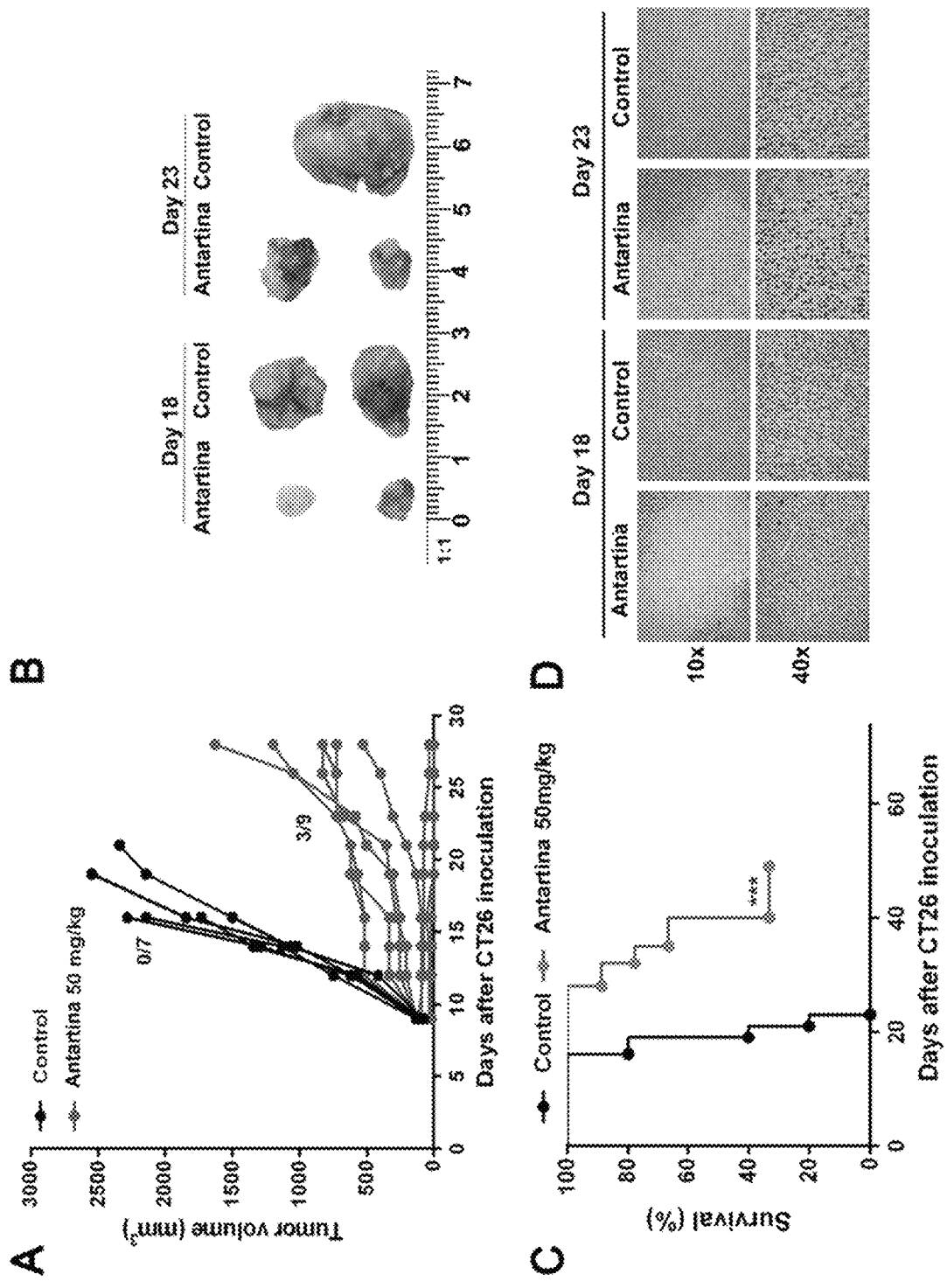

FIG. 6 shows higher doses of Antarina® exerted a potent antitumoral effect against CT26 CRC tumors. A) BALB/c mice were s.c. injected with $5\times10^5$ CT26 cells into the right flank (day 0) and tumors were allowed to reach 90 mm3 before treatment was started. Animals were distributed in groups: saline, Antarina® (50 mg/kg i.p., day 8 three times a week). Data are expressed as mean tumor volume. B) Representative macroscopic images of treated and untreated tumors at 18 and 23 days after CT26 cells inoculation. C) Representative image of H & E stained tumors from BALB/c mice treated or not with Antarina®; Antarina®-treated tumors showed intense mononuclear infiltrate and extensive areas of necrosis in comparison with saline; magnification of tumor regions (20×) Scale bar=50 μm. D) Animal survival (Kaplan-Meier, log rank test, $p<0.01$).

Figure 7:
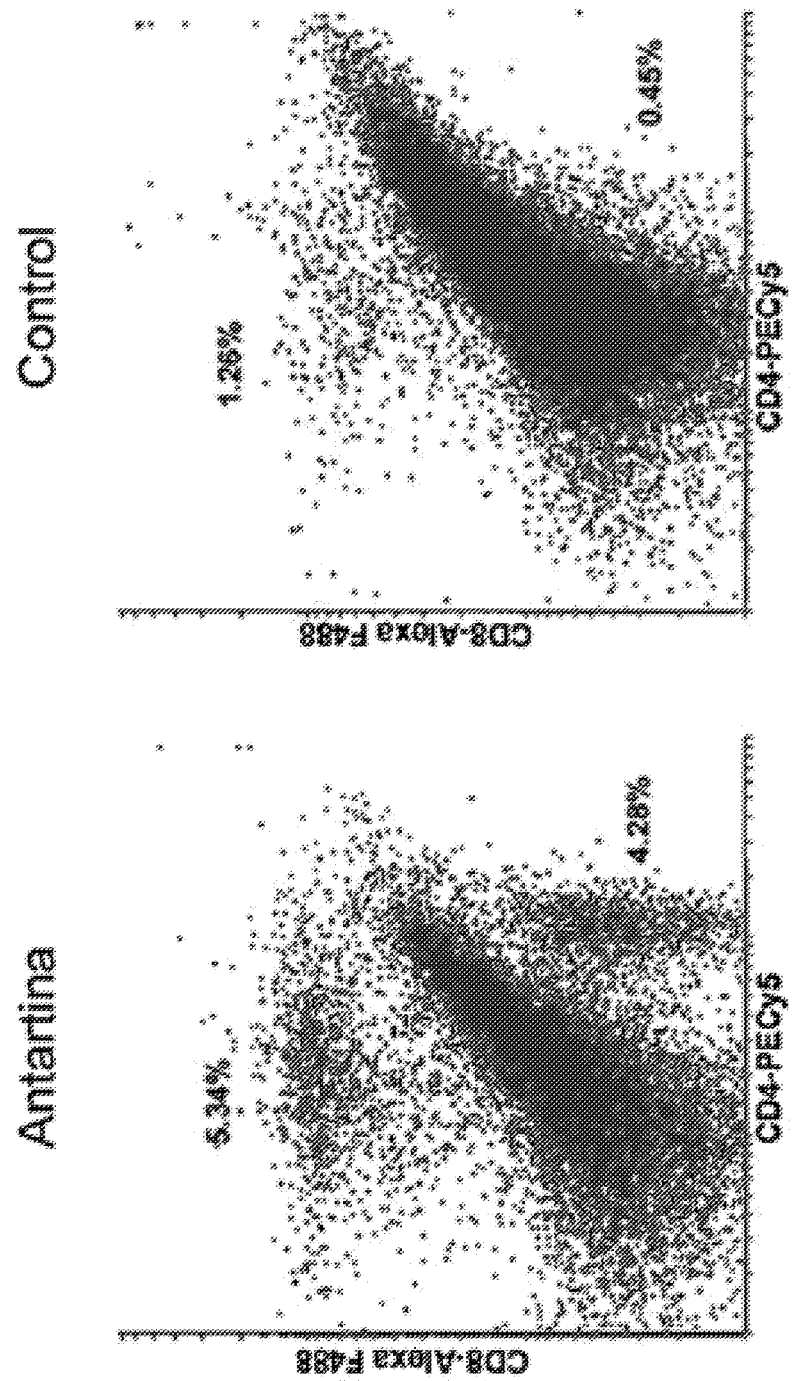
Figure 7:
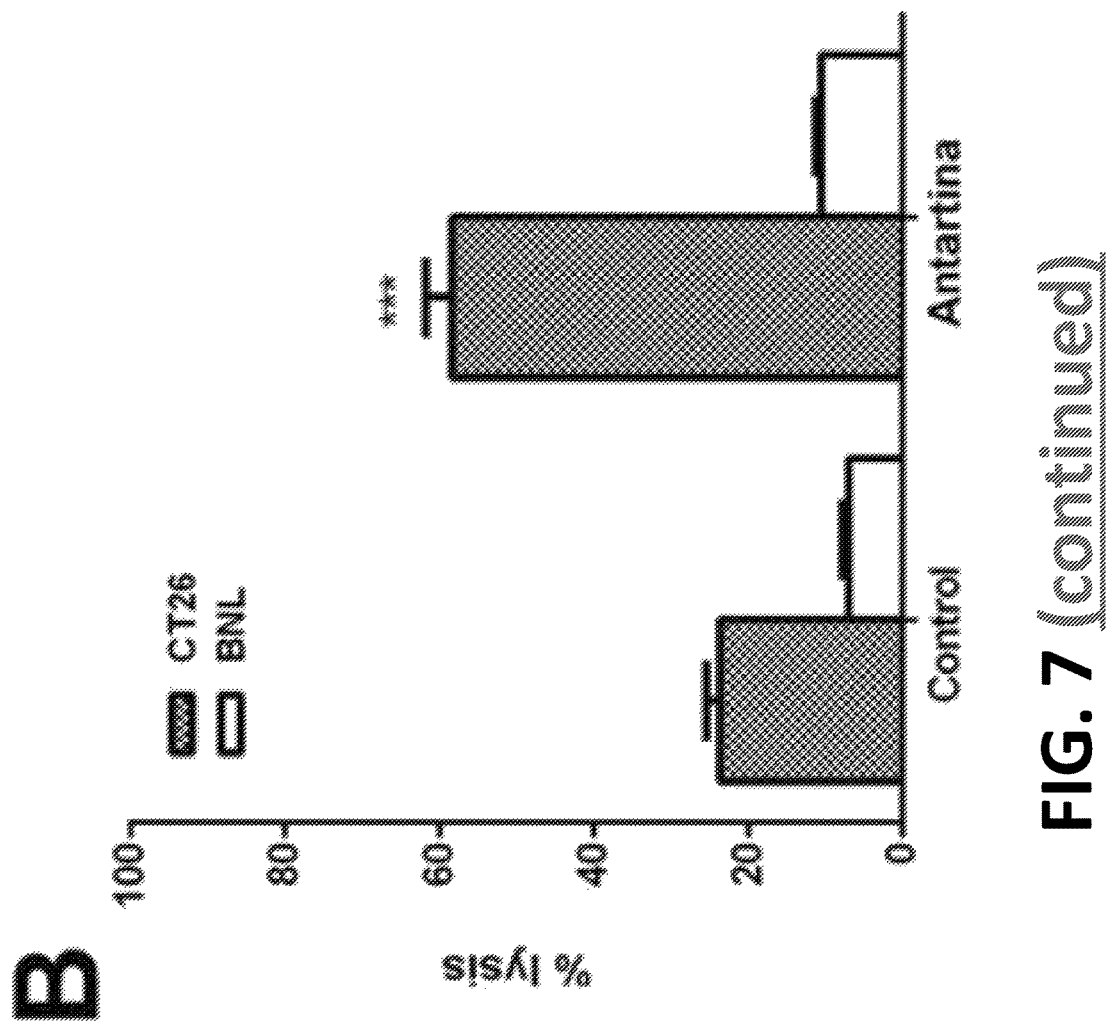
Figure 7:
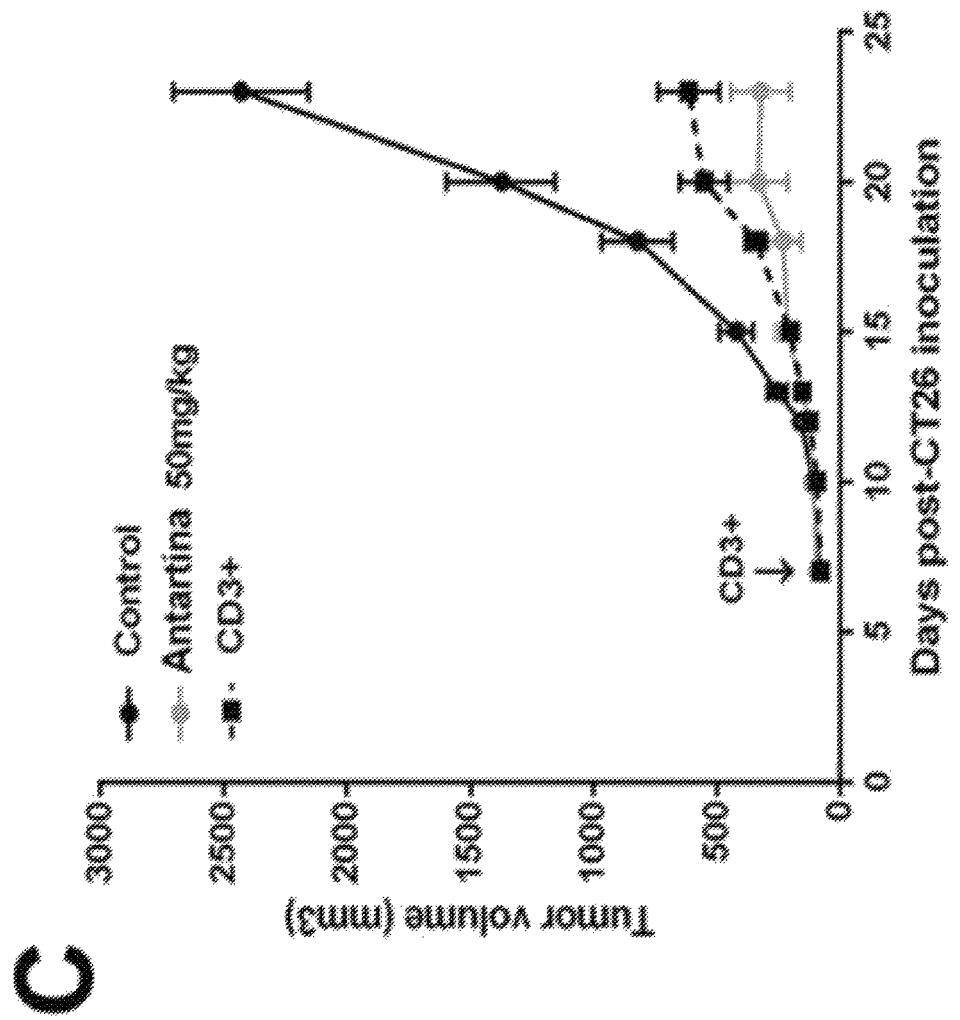
Figure 7:
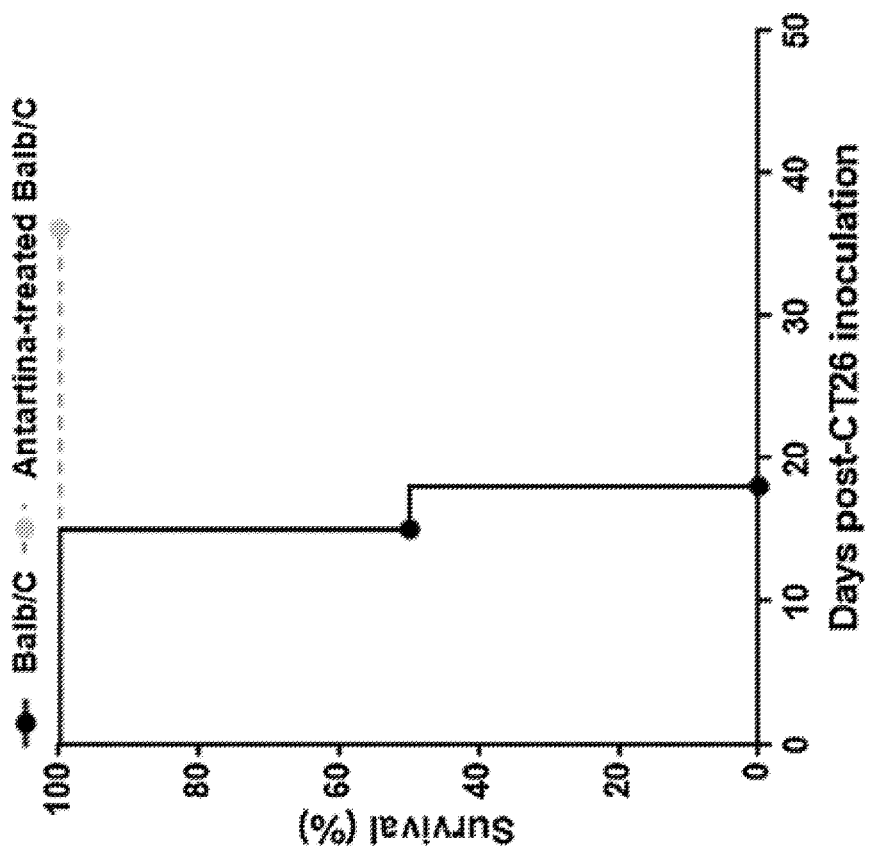
Figure 8:
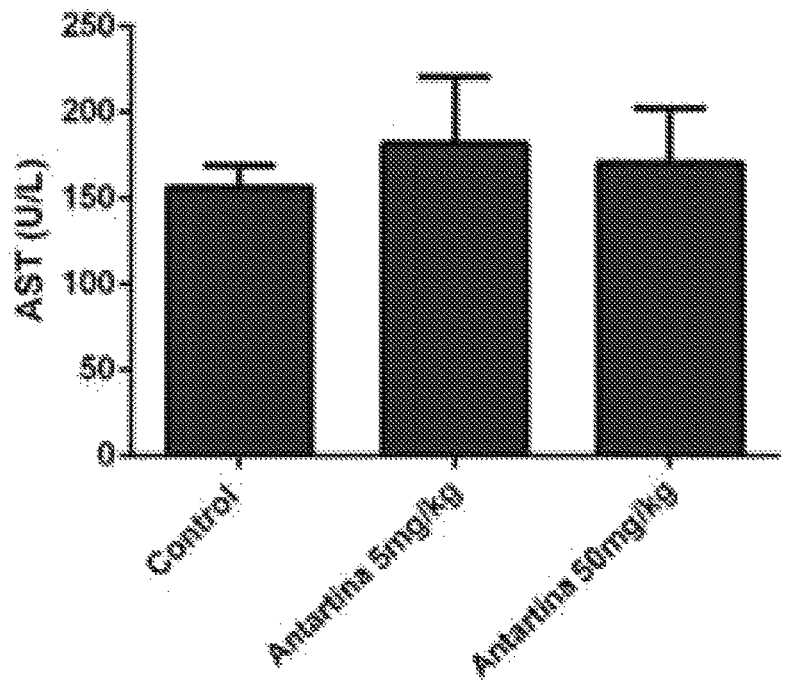
Figure 8:
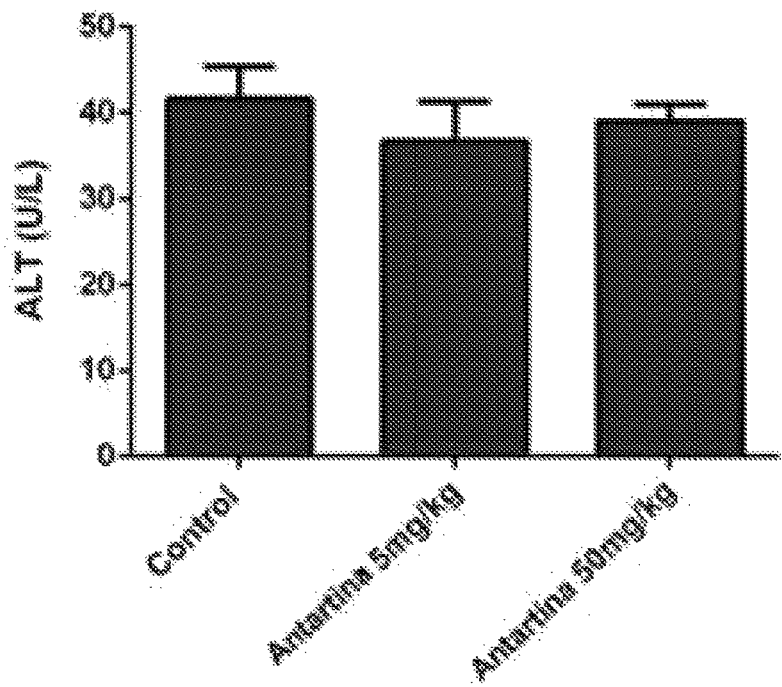
Figure 8:
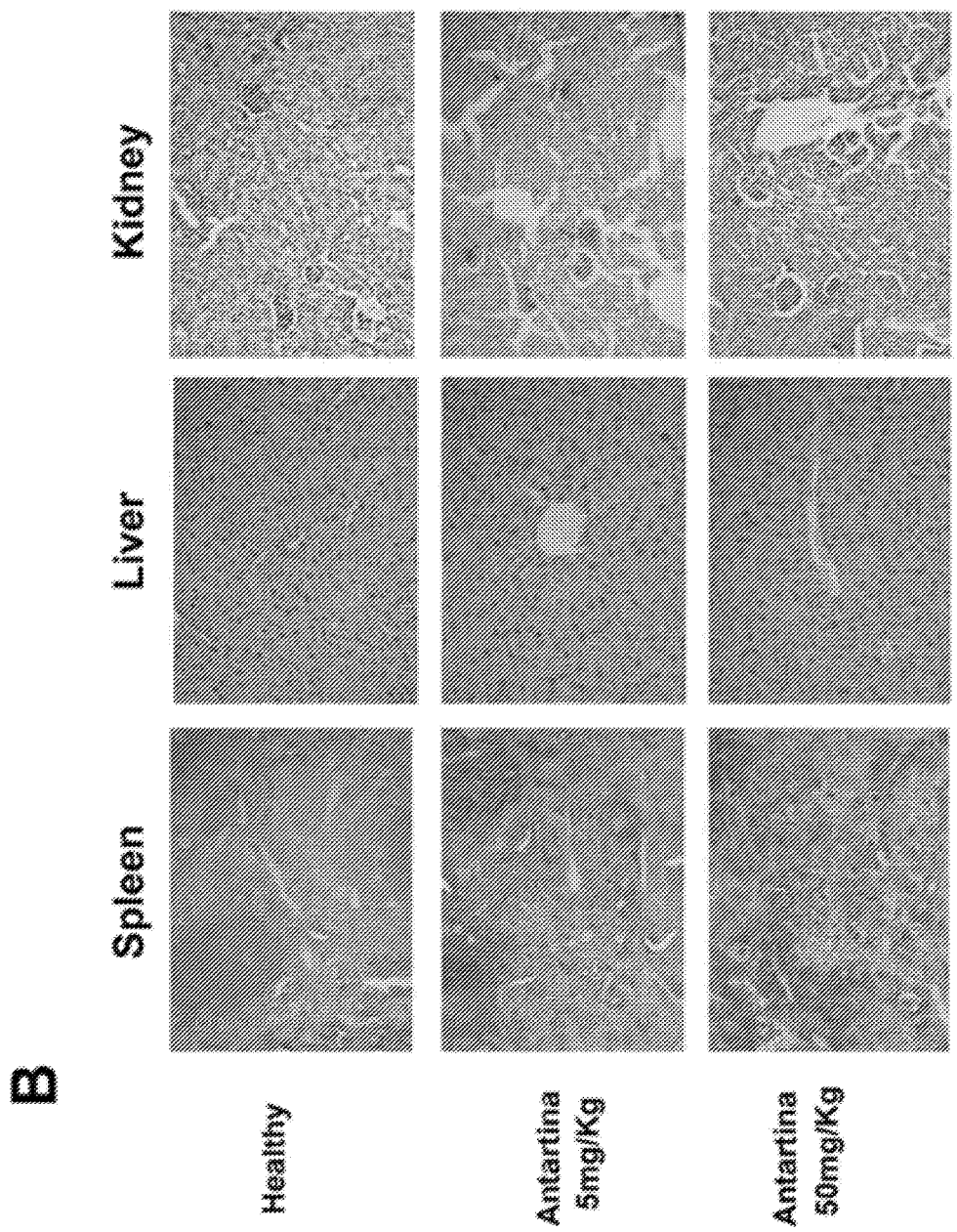

FIG. 7 shows Antarina® therapy induces antitumoral immunity. A) Percentage of tumor-infiltrating CD4+ and CD8+ T-lymphocytes *$p<0.05$ control vs. Antarina® on day 18, Mann-Whitney Test. B) Antarina® induces a potent specific cytotoxic T cell response against CT26 cells. Splenocytes derived from Antarina®-treated cured mice exerted a potent CTL activity against CT26 cells ***$p<0.001$ Saline vs. Antarina®. Student's T Test. C) Antitumoral effect of adoptively transferred CD3+ T cells on CT26 tumor-bearing mice. Adoptive transfer of specific CD3+ T cells induced a significant inhibition of tumor growth in comparison with control. Bars represent the average of measures of each group (n=6/group)±SEM *$p<0.05$. Kruskal-Wallis Test. D) Antarina® induces long-term antitumor immunity against CT26 CRC cells. Naive BALB/C and cured mice were re-challenged with $5\times10^5$ CT26 cells into the left flank. Results were expressed as the percentage of animal survival (Kaplan-Meier, log rank test, $p<0.05$); finally:

FIG. 8 a toxicology analysis. A) Liver transaminases aspartate aminotransferase (AST), alanine aminotransferase (ALT) were measured after Antarina® treatment. B) Representative H & E stained tissues from BALB/c mice untreated or 5 mg/kg and 50 mg/kg of Antarina® showing no signs of toxicity. Magnification of tumor regions (20×) Scale bar=50 μm.

PHARMACOMODULATION

Modulation of the product 9a was performed by maintaining the chromen-4-one moiety, and making variations in the sugar fragment.

On revising the bromo sugars available, in the FIG. 2, as compounds 11, from which the initial four are commercially available, and the last two have a synthesis described. The first compound is the fragment required to prepare the compound 9a as described.

From all those pyranosides, the corresponding flavonoids were obtained, as represented in FIG. 3, —where the representation of the sugar is in flat form to better differenciate the different fragments—. As previously indicated, the product 9a is the tricin 7-O-β-D-glucopyranoside described in the synthesis. The same procedure should be applied for 9b-9f preparation.

Material and Methods

Antartina

Tricin 7-O-β-D-glucopyranoside (Molecular formula: C21H20O10; CAS No. 32769-01-0, purity>99.2%) was detected and isolated from aqueous extracts of *Deschampsia antarctica* Desv. (Poaceae). Synthetic Antartina was supplied by the Centro de Química Aplicada y Biotecnología, Universidad de Alcalá. 28871 Alcalá de Henares, Madrid. Spain.

Cell Lines

Mouse CT26 tumor cell line, an undifferentiated murine colorectal carcinoma (CRC) cell line established from a N-nitroso-N-methylurethan-induced transplantable tumor in BALB/c (H-2d) mice and BNL hepatoma cell line was kindly provided by Prof. Jesús Prieto, University of Navarra, Spain. CT26 and BNL were cultured in complete DMEM (2 mM glutamine, 100 U/ml penicillin, 100 mg/ml streptomycin) and 10% heat-inactivated fetal bovine serum (FBS) and incubated at 37° C. in a 5% CO2 humidified atmosphere.

Animals

Six-to-eight-week-old male BALB/c mice were purchased from Fundación Balseiro, Buenos Aires, Argentina. Animals were maintained at our Animal Resources Facilities in accordance with the experimental ethical committee and the NIH guidelines on the ethical use of animals. The Animal Care Committee from School of Biomedical Sciences, Austral University, approved the experimental protocol.

Drugs

Antartina was dissolved in 0.1% DMSO and sterile water an injected intraperitoneally (i.p.) at the doses indicated or used for in vitro assays at different concentrations (0.1; 1 and 10 □g/ml). Fluorouracil Rontag® (5-Fu) 500 mg was diluted in saline solution at indicated concentrations (0.1; 1 and 10 □g/ml).

In Vitro Experiments

Cell Viability Assays:

CT26 cells were plated onto 96-well plates at a density of $5 \times 10^3$ cells/well and cultured with DMEM or Antartina at different doses (0.1-1-10 □at different doses (0.1-1-10 DMEM or y of 5×10t indicated concentrations (0.1; 1 and 10 nd 10 ions (0.1; 1 and 10 mental for 4 hour after which the absorbance of each well was read at 490 nm. All assays were performed in quadruplicate, and each assay was repeated twice.

Cell Cycle Analysis:

$1 \times 10^6$ CT26 cells cultured with DMEM or Antartina were collected washed in PBS and fixed in a mixture of ice-cold 70% (v/v) ethanol, FBS and distill water. Fixed cells were centrifuged and stained with propidium iodide (PI) solution (50 μg/ml PI, 180 U/ml RNAse). DNA content was determined using a FACS Accuri 6 laser flow cytometer (Becton Dickinson).

In Vivo Experiments

Subcutaneous CRC model: CT26 cells were injected at a dose of $5 \times 10^5$ cells subcutaneously (s.c.) into the right flank of BALB/c mice (day 0). Tumors were allowed to reach approximately 90 mm³ in size before treatment was started. Animals were distributed in different groups and then treated with Antartina or 0.1% DMSO in sterile water intraperitoneal (i.p.) (control group, n=6); Antartina (5 or 50 mg/kg i.p., day 8, n=9). Tumor growth was assessed by caliper measurement.

Liver Metastatic CRC Model:

BALB/c mice received an intra-hepatic inoculation of $5 \times 10^5$ CT26 cells (day 0). The mice were distributed in experimental groups and treated with saline (control group, n=6); Antartina (5 mg/kg i.p., n=8 day 8). At day 18, animals were sacrificed and the volume of metastatic nodules was measured with caliper.

Adoptive T Cell Therapy:

CT26 tumor bearing mice were inoculated with $1 \times 10^6$ CD3$^+$ T cells isolated by magnetic cell sorting as it was described above. Untreated and Antartina-treated mice that not received CD3$^+$ T cells were used as control groups. Tumor growth was assessed by caliper measurement.

Long-Term Protection Study:

to evaluate protective immunity, animals that were free of disease at 3 wk after complete regression of primary tumors (7 week after first tumor inoculation) were challenged with $5 \times 10^5$ CT26 cells on the left flank.

Ex Vivo Experiments

Histology:

tumor samples from experimental groups were obtained 10 and 15 days after treatment and fixed in 10% phosphate-buffered formalin. Five-micrometer sections from paraffin-embedded tissues were stained with hematoxylin and eosin (H & E) for histologic examination.

Flow Cytometry Analyses:

previously, single cell suspensions were obtained by mechanical disruption of tumor samples treated with 0.5 mg/ml Collagenase I at 37° C. for 45 min and washed with PBS 1% bovine serum albumin. Then, tumor cells were stained with PECy5-anti-CD4 (BD Biosciences) and AlexaFluor488-anti-CD8 (BD Biosciences) and their respective isotypes and subjected to flow cytometry (FACSAria, BD). Data were analyzed using Cyflogic v. 1.2.1 software.

Isolation of CD3$^+$ T Lymphocytes:

BALB/c mice were injected with CT26 cells and treated with Antarina as described above. Splenocytes from cured mice were isolated and pooled and $2 \times 10^6$ cells/ml was co-cultured with mitomycin C-treated CT26 cells ($2 \times 10^5$/ml) in a 24-well plate (1 ml/well) with mouse recombinant IL-2 (10 U/ml). Seven days later, viable cells were harvested and washed, adjusted to $2 \times 10^6$/mL, and co-cultured again with mitomycin C-treated CT26 cells in presence of 10 UI/ml IL-2. The cytotoxic activity of harvested cells was confirmed with the LDH Cytotoxicity Detection Kit. On day 14, viable cells were used for isolation of CD3$^+$ T Lymphocytes using anti-mouse CD3$^+$ MicroBeads and magnetic cell sorting following the manufacturer's recommendations (Miltenyi Biotec).

Cytotoxicity Assay:

viable splenocytes from control or treated mice ($10 \times 10^6$) were stimulated in vitro with mitomycin C-treated CT26 cells ($10 \times 10^5$ cells/well in 24-well-plates). On day 5, cells were harvested and washed, adjusted to $2 \times 10^6$/mL, and added to 96-well-plate (effector cells). To determine specific CTL cytotoxicity activity CT26 and BNL cells were used as target at $2 \times 10^5$/mL. After incubation for 4 h at 37° C., plates were centrifuged and cell-free supernatants were obtained. Levels of released LDH were evaluated with the LDH Cytotoxicity Detection Kit (Sigma-Aldrich) following the manufacturer's instructions and expressed as percentage of lysis.

Toxicity Studies:

BALB/c mice untreated or treated with Antartina (5 mg/kg and 50 mg/kg) were used to assess its toxicology profile. Mice were observed for more than 30 days. Aspartate aminotransferase (AST) and alanine aminotransferase (ALT) levels were measured by standard colorimetric methods. Also, healthy mice or mice receiving Antartina were sacrificed to collect liver, spleen, and kidney samples. Paraffin embedded tissues were stained with H & E for pathological analysis.

Statistic Analysis

All experiments were repeated at least three times. Values were expressed as the mean±SEM. The Student's T Test, Mann-Whitney Test or ANOVA with Tukey's test were used to evaluate the statistical differences between two groups or more than two groups. Mice survival was analyzed by a Kaplan-Meier curve. A p value of <0.05 was considered as significant. Prism software (Graph Pad, San Diego, Calif., USA) was employed for the statistical Results and Discussion Antartina has been detected and isolated from aqueous extracts of *Deschampsia antarctica* Desv. (Poaceae), shows the molecular structure of tricin 7-O-β-D-glucopyranoside. It has been reported that tricin, a natural flavone and its derivative compounds exerts antioxidative effects and exhibits antiproliferative activity in tumor cells. Then, we decided to assess the effect of the tricin-O-glucoside Antartina on in vitro cultured murine CT26 CRC cell line. For this purpose, CT26 cells were incubated with increasing doses of Antartina for 24, 48 and 72 h. As a result, we found that Antartina inhibits CT26 cell survival at 48 h at the highest concentration (p<0.05, FIG. 4A). Additionally, cell viability was reduced at 72 h to almost 50% at 10 □g/ml of Antartina, and more than 20% at the dose of 1 □g/ml (p<0.001 and p<0.05, respectively). When compared with fluorouracil (5-Fu), the most widely used anticancer agent for advanced CRC patients, Antartina exhibited similar strength to decrease CT26 cell viability (FIG. 4B). The effect of cancer chemotherapy has been associated to cytotoxic mechanisms, resulting in the inhibition of tumor growth[11,12]. For instance, folate metabolism disruption in cancer cells causes ineffective DNA synthesis and cell cycle alteration[11]. In this sense, tricin also showed capability to block cell cycle progression in hepatic stellate cells and cancer cell lines[8,13]. To examine whether Antartina might affect cell cycle, CT26-treated cells were stained using propidium iodide and analyzed by flow cytometry. The cell cycle pattern showed that CT26 cells were arrested at $G_2/M$ phase both at 48 h and 72 h after incubation with 10 □g/ml of Antartina (p<0.05) (FIG. 4C) Similar results were obtained when cell cycle analysis was performed 48 h and 72 h after treatment with 5-Fu (p<0.05, FIG. 4D).

In view of the remarkable cytotoxic effect on CRC cells observed in vitro, we next tested the capability of Antartina to exert antitumor activity in in vivo experiments. To this end, BALB/c mice were subcutaneously (s.c.) inoculated with CT26 tumor cells, and treatments were initiated when tumors reached a tumor volume ~90 mm³. Over the course of 30 days, CT26 tumor-bearing mice treated with Antartina showed a significant inhibition of tumor growth in comparison with the saline control group (FIG. 5A) Importantly, the survival rate of mice receiving Antartina was significantly increased compared with controls (p<0.01) (FIG. 5B).

We also challenged Antartina anticancer activity in a metastatic CRC model. For this purpose, CT26 cells were injected into the liver of mice by laparotomy (day 0) and then treated with Antartina at a dose of 5 mg/kg on day 8. FIG. 5C showed mean tumor size at day 18 after CT26 cells inoculation. Interestingly, Antartina exerted a potent antitumor effect in comparison with control group (mean of tumor volume 955±275 mm³ vs. 1508±204 mm³, respectively); in addition, more than 60% of Antartina treated-animals showed a reduction in metastases growth. More importantly, survival of mice treated with Antartina was superior in comparison with controls (FIG. 5D; p<0.01).

Studies were conducted to test higher doses of Antartina. To this end, CT26 CRC cells were s.c. injected into BALB/c mice (day 0). On day 8, nodules reaching 90 mm³ in size received 50 mg/kg of Antartina or saline. A potent tumor volume reduction was obtained with Antartina, and complete tumor regression was achieved in more than 30% of mice (3/9) (FIG. 6A). Tumor progression was evaluated at different time points (10 and 15 days after treatment) as shown in FIG. 6B. Microscopic examination of tumor sections showed extensive areas of necrosis and marked mononuclear cells infiltration in tumors treated with Antartina (FIG. 6C). In addition, animal survival was significantly increased in Antartina-treated mice compared to the saline control group (FIG. 6D; p<0.01).

In addition, we evaluated the toxicology profile of Antartina therapy (at the doses of 5 and 50 mg/kg) in mice. We found that all animals remained healthy throughout the experimental protocol; body weight gain in both groups of mice was similar during the observed period. Therefore, Antartina was well tolerated with no evident signs of clinical and biochemical toxicity within the studied period of time (FIG. 7).

In view of the marked presence of mononuclear cells infiltrate within Antartina-treated tumors, we analyzed the prevalence of T lymphocytes in tumor samples by flow cytometry and detected an increased proportion of tumor-infiltrating $CD4^+$ and $CD8^+$ T cells in Antartina-treated mice in comparison with control group (p<0.05; FIG. 8A). More importantly, Antartina was found to elicit a potent activation of specific cytotoxic T lymphocytes (CTLs) against CT26 cells (FIG. 8B; p<0.001); no CTL activity was observed against hepatocellular carcinoma cells (BNL cells) in vitro, although preliminary experiments revealed that Antartina has antitumoral activity in vivo against hepatocellular carcinoma established in mice with advanced fibrosis (data not shown). Interestingly, when specific CTLs were adoptively transferred into CT26-tumor bearing mice, a significant inhibition of tumor growth was achieved compared with controls (FIG. 8C). Our results strongly suggest that the potent antitumor effect induced by Antartina is mediated, at least in part, by the induction of antitumor immunity against CT26 CRC. To further investigate whether Antartina can induce memory immune response, cured animals were re-challenged with CT26 CRC cells 3 weeks after complete tumor regression. FIG. 8D shows that CT26 cells were rejected in all animals of the Antartina group; on the contrary, tumor grew in all mice in the control group. These data indicate that Antartina has the ability to induce a long-term protection against tumor recurrence.

Although flavonoids have been reported to have a wide range of biological activities, information regarding to immunostimulation properties are scarce. However, it has been recently reported that salvigenin, a polyoxygenated flavone, stimulates an immune response leading to the inhibition of tumor growth in a mouse model of breast cancer[14]. The present work synthetized a tricin derivative called Antartina that induces a potent stimulation of the immune system leading to complete tumor regression in more than 30% of mice and a long-lasting antitumor immunity. This study provides strong evidence of the immunostimulatory properties of Antartina. Therefore, Antartina deserves further evaluation as a potential anticancer molecule for patients with advanced CRC.

REFERENCES

1. Ferlay J., E. M., Dikshit R., Eser S., Mathers C., Rebelo M., Parkin D. M., Forman D., Bary F., Cancer Incidence and Mortality Worldwide: Iarc Cancer Base. International Agency for Research on Cancer *International Agency for Research on Cancer* (2012).
2. Prieto, J., Qian, C., Sangro, B., Melero, I. & Mazzolini, G. Biologic therapy of liver tumors. *Surg Clin North Am* 84, 673-696, doi:10.1016/S0039-6109(03)00230-5 (2004).
3. Alberdi, M., Bravo, L. A., Gutierrez, A., Gidekel, M. & Corcuera, L. J. Ecophysiology of *Antarctic* vascular plants. *Physiol Plant* 115, 479-486 (2002).
4. Cavicchioli, R., Siddiqui, K. S., Andrews, D. & Sowers, K. R. Low-temperature extremophiles and their applications. *Curr Opin Biotechnol* 13, 253-261 (2002).
5. Bravo, L. A. & Griffith, M. Characterization of antifreeze activity in *Antarctic* plants. *J Exp Bot* 56, 1189-1196, doi:10.1093/jxb/eril 12 (2005).
6. van de Staaij, J. et al. Flavonoid concentrations in three grass species and a sedge grown in the field and under controlled environment conditions in response to enhanced UV-B radiation. *J Photochem Photobiol B* 66, 21-29 (2002).
7. Mi Li, Y. P., Chang Geun Yoo and Arthur J. Ragauskas. The occurrence of tricin and its derivatives in plants. *Green Chem* 18 (2016).
8. Cai, H. et al. Growth-inhibitory and cell cycle-arresting properties of the rice bran constituent tricin in human-derived breast cancer cells in vitro and in nude mice in vivo. *Br J Cancer* 91, 1364-1371, doi:10.1038/sj.bjc.6602124 (2004).
9. Hudson, E. A., Dinh, P. A., Kokubun, T., Simmonds, M. S. & Gescher, A. Characterization of potentially chemopreventive phenols in extracts of brown rice that inhibit the growth of human breast and colon cancer cells. *Cancer Epidemiol Biomarkers Prev* 9, 1163-1170 (2000).
10. Oyama, T. et al. Dietary tricin suppresses inflammation-related colon carcinogenesis in male Crj: CD-1 mice. *Cancer Prev Res (Phila)* 2, 1031-1038, doi:10.1158/1940-6207.CAPR-09-0061 (2009).
11. Longley, D. B., Harkin, D. P. & Johnston, P. G. 5-fluorouracil: mechanisms of action and clinical strategies. Nat Rev Cancer 3, 330-338, doi:10.1038/nrc1074 (2003).
12. Chabner, B. A. & Roberts, T. G., Jr. Timeline: Chemotherapy and the war on cancer. *Nat Rev Cancer* 5, 65-72, doi:10.1038/nrc1529 (2005).
13. Seki, N. et al. Tricin inhibits proliferation of human hepatic stellate cells in vitro by blocking tyrosine phosphorylation of PDGF receptor and its signaling pathways. *J Cell Biochem* 113, 2346-2355, doi:10.1002/jcb.24107 (2012).
14. Noori, S., Hassan, Z. M., Yaghmaei, B. & Dolatkhah, M. Antitumor and immunomodulatory effects of salvigenin on tumor bearing mice. *Cell Immunol* 286, 16-21, doi: 10.1016/j.cellimm.2013.10.005 (2013).

The invention claimed is:

1. An in situ method of inhibiting tumor growth in mouse CT 26 colon carcinoma cell lines comprising injecting said cell lines with a solution of a Tricin pyranoside compound said Tricin pyranoside compound selected from the group consisting of Tricin-7-O-beta-D-glucopyranoside 9a, Tricin-7-O-beta-D-galactopyranoside 9b, Tricin-7-O-beta-D-mannopyranoside 9c, Tricin-7-O-beta-D-talopyranoside 9d, Tricin-7-O-beta-D-idopyranoside 9e and Tricin-7-O-beta-D-allopyranoside 9f; followed by the steps of quantitatively observing the resulting reduction in cell counts and comparing said observation with a controlled experiment.

2. An in vivo method of inhibiting tumor growth and metastases inducing complete tumor regression and increasing animal/mammal survival in live mammals comprising injecting said mammal with a solution of a Tricin pyranoside compound said Tricin pyranoside compound selected from the group consisting of Tricin-7-O-beta-D-glucopyranoside, Tricin-7-O-beta-D-galactopyranoside, Tricin-7-O-beta-D-mannopyranoside, Tricin-7-O-beta-D-talopyranoside, Tricin-7-O-beta-D-idopyranoside and Tricin-7-O-beta-D-allopyranoside.

3. The method according to claim 2 wherein said mammal is a mouse.

* * * * *